United States Patent [19]

Nappier

[11] Patent Number: 5,210,245

[45] Date of Patent: May 11, 1993

[54] GOLD CARBOXYLATES AND PROCESS FOR PREPARING THE SAME

[75] Inventor: Thomas E. Nappier, Parma, Ohio

[73] Assignee: Mooney Chemicals, Inc., Cleveland, Ohio

[21] Appl. No.: 852,673

[22] Filed: Mar. 17, 1992

Related U.S. Application Data

[62] Division of Ser. No. 624,652, Dec. 10, 1990.

[51] Int. Cl.$^5$ ............................................... C07F 1/12
[52] U.S. Cl. ..................................... 556/114; 556/115
[58] Field of Search ................................. 556/114, 115

[56] References Cited

U.S. PATENT DOCUMENTS

| | | | |
|---|---|---|---|
| 2,044,968 | 6/1936 | Bruson | 260/11 |
| 2,087,999 | 7/1937 | Salzberg | 260/11 |
| 2,383,647 | 8/1945 | Hauser | 117/123 |
| 2,910,377 | 10/1959 | Owen | 117/36 |
| 3,255,222 | 6/1966 | Horowitz | 260/414 |
| 3,687,993 | 8/1972 | Hornig et al. | 260/430 |
| 3,700,458 | 10/1972 | Tindhalm | 96/114.1 |
| 4,307,187 | 12/1981 | Ikenoue et al. | 430/619 |

OTHER PUBLICATIONS

International Search Report PCT/US91/08792.
Chemical Abstracts, Chemistry of Synthetic High Polymers vol. 109, No. 18, Oct. 31, 1988, pp. 1 and 889.
English language abstract of Sharma et al, "Preparation of Some Bisoxime Palladium Dichlorides, Etc." Kogyo Kagaku Zasshi, vol. 72(7), pp. 1549-1551 Japan 1966 in Chemical Abstracts, vol. 72(1970), Abstract No. 17996P.
English language abstract of Japanese laid open patent application (Kokai) No. 64-000177 published in Japanese Patent Abstracts (unexamined) 1989, vol. 89, No. 7, GpG, 30.

*Primary Examiner*—José G. Dees
*Assistant Examiner*—Porfirio Nazario
*Attorney, Agent, or Firm*—Renner, Otto, Boisselle & Sklar

[57] ABSTRACT

Gold carboxylates and a process for preparing gold salts of organic carboxylic acids are described. The gold carboxylates are represented by the formula $$Au_x(R(\overset{\overset{\displaystyle O}{\|}}{C}-O)_y)_z \quad (I)$$

in which R represents hydrogen or an organic group of valence y and x, y and z each represent a positive integer such that $x = y \cdot z/3$. The process comprises reacting an alkali or alkaline earth metal salt of an organic carboxylic acid with a gold salt in an organic liquid which at least partially dissolves the alkali and/or alkaline earth metal salt, the gold salt, and the desired gold carboxylate product, but is not a solvent for the salt formed between the alkali or alkaline earth metal and the anion of the gold salt.

25 Claims, No Drawings

GOLD CARBOXYLATES AND PROCESS FOR PREPARING THE SAME

This is a division, of application Ser. No. 07/624,652, filed Dec. 10, 1990, now allowed.

TECHNICAL FIELD OF THE INVENTION

The present invention relates to novel gold carboxylates and methods for preparing gold carboxylates.

BACKGROUND OF THE INVENTION

Many types and mixtures of metal salts and soaps of natural or synthetic organic acids, particularly carboxylic acids, have been suggested and commercially offered over several decades. These have been used to supply metals in forms which are soluble in organic liquids, particularly in various hydrocarbon oils and solvents, to form solutions having various desired properties and uses. For example, such metal salts have found uses as catalysts and as fuel and lubricant additives. Metal salts of carboxylic acids also are useful as stabilizers for various polymers including polyvinyl chloride-type plastics, and in the area of drying catalysts for paints, varnishes and other coating compositions.

However, since gold is the most noble of the noble metals, gold is not dissolved by most acids under ordinary conditions. Gold complexes, such as chloroauric acid formed by the reaction of gold with aqua regia (3:1 hydrochloric:nitric acid), and alkali (dicyano)gold(I) formed by a reaction between gold and an alkaline cyanide solution in the presence of air or hydrogen peroxide, are compounds generally bound more strongly to the respective anions than the ligands produced between gold and carboxylates, making it difficult to separate gold carboxylates from a solution containing these other ligands. These other ligands are considered undesirable in a number of applications in which gold carboxylates would be desired.

For example, the catalytic and co-catalytic properties of gold may be inhibited by the presence of chloride ions or chlorine-containing compounds, such as when gold is used as a catalyst for the production of phenol acetate. Nitrogen compounds such as amines, amides and cyanides; phosphorus compounds such as phosphate, phosphine complex compounds; and sulfur compounds such as sulfates, sulfones, sulfoxides and sulfides may also act as a catalyst poison. The cyanides, of course, are also undesirable from a human toxicological viewpoint.

U.S. Pat. No. 3,687,993 to Hornig, deceased, et al describes a process for making solid gold hydroxy diacetate of the formula $Au(OH)(O_2CCH_3)_2$ and its use as a catalyst or catalyst component for homogeneous or heterogeneous reactions. It is also mentioned that the gold hydroxy diacetate may be used for manufacture of other organic gold compounds such as reacting it with propionic acid, or with other carboxylic acids, to yield a corresponding gold compound.

Takiguchi et al, "Synthesis of naphthenates of gold, silver, platinum and palladium and bisoxime palladium dichlorides," Kagyo Kagaku Zasshi, Vol. 72, No.7, (Japan 1969) pp. 1549-1551, describes reactions of chloroauric acid and chloroplatinic acid with sodium naphthenate, and reports that the direct reaction between an aqueous solution of chloroauric acid and sodium naphthenate lacked reproducibility and yield and the direct reactions between chloroplatinic acid and sodium naphthenate caused marked precipitation of metal and "did not produce a good result."

U.S. Pat. No. 3,700,458 (Lindholm) describes a chemical process for preparing noble metal salts of carboxylic acids useful in photosensitive and thermosensitive compositions. The process involves mixing a non-aqueous solution of an organic carboxylic acid with a non-aqueous solution of a noble metal trifluoroacetate or tetrafluoroborate in the presence of an organic peptizer. A variety of organic peptizers are disclosed including polyvinyl acetals and certain acrylate copolymers.

As far as the inventor is aware, none of the foregoing processes provides a facile means for obtaining gold carboxylates, particularly gold carboxylates derived from carboxylic acids having a molecular weight higher than acetic acid.

SUMMARY OF THE INVENTION

The present invention relates to gold carboxylate products and a process for preparing gold salts of organic carboxylic acids. The process comprises reacting an alkali or alkaline earth metal salt of an organic carboxylic acid with a gold salt in an organic liquid at a temperature sufficient to form the desired organic gold carboxylate. Preferred organic liquids are ones which are solvents for the alkali or alkaline earth metal carboxylate and the gold salt, but which are not solvents for a salt formed between the alkali or alkaline earth metal of the starting carboxylate and the anion of the gold salt. The process of the present invention results in the formation of the desired gold carboxylates which generally are characterized as high purity products. The products may be recovered as a filtrate and further purified by redissolving the product in a second organic liquid. The second organic liquid is preferably different from the organic liquid used during the above reaction procedure.

Solutions prepared from the gold carboxylates have numerous uses. They are useful as homogeneous catalysts and they may serve as starting materials for making printed circuits, electrical contacts, and hybrid interconnects for electronic devices, electrodes, decorative coatings on glass and ceramics, reflective coatings for optical surfaces, pharmaceuticals, etc.

DESCRIPTION OF THE PREFERRED EMBODIMENTS

Gold carboxylates of the present invention may be described by reference to the following formula:

wherein each R independently represents a hydrogen atom or an organic group of valence y and x, y and z each represent a positive integer such that $x=y\cdot z/3$. The organic group R may be any group containing predominantly carbon and hydrogen atoms and may comprise one or more hetero atoms such as nitrogen, oxygen, sulfur and/or halogen. Preferably, R comprises less than ten mole-percent hetero atoms. More preferably, R does not contain any hetero atoms or contains only oxygen atoms as hetero atoms. Examples of R groups include aliphatic, alicyclic and aromatic mono- and polyvalent moieties. The aliphatic moieties contain from 1 to about 29 carbon atoms, the alicyclic moieties contain from 4 to about 29 carbon atoms, and the aromatic moieties contain from 6 to about 29 carbon atoms. Generally, the aliphatic moieties will generally contain at least about 3 carbon atoms, and will preferably contain at least about 5 carbon atoms, and more preferably at least about 7 carbon atoms and will preferably contain up to about 17 carbon atoms, more preferably up to about 11 carbon atoms and even more preferably up to about 9 carbon atoms.

Examples of organic R groups include methyl, ethyl, propyl, butyl, isobutyl, pentyl, isopentyl, hexyl, 2-ethylbutyl, benzyl, nonyl, isononyl, decyl, neodcyl, dodecyl, palmityl, stearyl, oleyl, linolyl, etc.

In one embodiment of the present invention, x represents 1. Specific examples of such gold carboxylates include gold 2-ethylhexanoate, gold octanoate, gold isooctanoate, gold decanoate, gold neodecanoate, etc.

The process for preparing the gold carboxylates in accordance with the present invention comprises, in one embodiment, the steps of (A) preparing a mixture of (1) at least one alkali or alkaline earth metal salt of an organic carboxylic acid, (2) at least one gold salt having an anion other than the carboxylate anion of (A)(1), and (3) an organic liquid capable of at least partly dissolving the at least one alkali or alkaline earth metal salt of an organic carboxylic acid of (1) and the at least one gold salt of (2), which is not a solvent for a salt formed between the alkali or alkaline earth metal of (1) and the anion of (2); and (B) maintaining the mixture (A) at a temperature below the decomposition temperature of components (A)(1), (A)(2) and (A)(3) and gold carboxylate product for a period of time sufficient to form the gold carboxylate.

The gold salt may be selected from any which have an anion capable of forming an alkali or alkaline earth metal salt of (A)(1) which is insoluble in the organic liquid. Examples include gold chlorides, such as gold trichloride and tetrachloroauric acid; nitrates; sulfates; and bromides, such as gold tribromide.

As noted, the preparation of the gold carboxylates by the process of the present invention is conducted in an organic liquid which can be any organic liquid in which the alkali or alkaline earth metal salts derived from the alkali or alkaline earth metal carboxylate and the gold salt are relatively insoluble. Examples of organic liquids which can be utilized in the process of the present invention include carboxylic acids or anhydrides such as acetic acid, propionic, butyric acid, 2-ethylhexanoic acid, decanoic acid, isooctonoic acid, isononanoic acid, neodecanoic acid, dodecanoic acid, etc.; esters and ester-acids of carboxylic acids or anhydrides such as methyl acetate, ethyl acetate and diethyl acetate; ketones such as acetone and methyl ethyl ketone; hydroxy-containing organic compounds including saturated aliphatic alcohols such as methanol, ethanol, propanol, and butanol, unsaturated aliphatic alcohols such as allyl alcohol, etc.; aromatic solvents including benzene, toluene, xylene, cumene, psuedo cumene and mesitylene; saturated ethers, e.g., saturated aliphatic ethers such as di-n-propyl ether or di-isopropyl ether or a cyclic ether such as tetrahydrofuran (THF) or dioxane; nitrile solvents such as acetonitrile; halocarbons such as methylene chloride or dichloroethane; etc. Among these, the carboxylic acids or anhydrides, ketones, saturated aliphatic alcohols, aromatic solvents, saturated aliphatic ethers, and cyclic ethers are preferred, and among these, acetone, methyl ethyl ketone, propanol, xylene and THF are preferred.

The alkali or alkaline earth metal salts of organic carboxylic acids from which the gold salts can be prepared include salts of various single- and multivalent hydrocarbon groups having one or more carboxy group substituents such as unsubstituted, substituted, or polyfunctional aliphatic, alicyclic and aromatic mono- and polybasic carboxylates. The organic carboxylates may be either natural or synthetic, or mixtures thereof. Functional moieties include ether, ester, thioester, ketone, amine, nitrile, and heterocyclic linking groups and substituents. Examples of alkali or alkaline earth metal salts of natural acids, although usually refined, include alkali or alkaline earth metal salts of straight- and branched-chain carboxylic acids, including mixtures such as tall oil acids, and alkali or alkaline earth metal salts of cyclic carboxylic acids such as naphthenates. A variety of synthetic carboxylates, and particularly aliphatic carboxylates or mixtures thereof, are useful. The aliphatic carboxylates used in the present invention contain at least 1 carbon atom, and generally at least 2 carbon atoms and may contain up to about 30 carbon atoms or more. The alicyclic carboxylates can contain from 5 to about 30 carbon atoms. Aromatic carboxylates contain from 7 to about 30 carbon atoms. The alkali metal carboxylates are generally preferred for the low solubility of the alkali metal halides in many organic liquids.

Generally, the aliphatic carboxylates will contain at least 4 carbon atoms, preferably contain at least about 6 and more preferably at least about 8 carbon atoms and in general up to about 18 carbon atoms, more preferably up to about 12 carbon atoms and even more preferably up to about 10 carbon atoms. In one embodiment, at least about 80 weight-percent of the organic carboxylate are these preferred aliphatic carboxylates. When metal salts comprising more than one carboxylic acid are employed, the metal salts of carboxylic acids containing, for example, at least about six carbon atoms may be employed advantageously in combination with metal salts of carboxylic acids having as few as two carbon atoms as one of the acids of the metal salt mixture.

Examples of useful organic carboxylates include alkali and alkaline earth metal salts of acetic acid, propionic acid, butyric acid, isopentanoic acid, hexanoic acid, 2-ethyl butyric acid, benzoic acid, nonanoic acid, decanoic acid, 2-ethyl hexanoic acid, isooctanoic acid, isononanoic acid, neodecanoic acid, dodecanoic acid, lauric acid, palmitic acid, stearic acid, oleic acid, linoleic acid, commercially available mixtures of two or more carboxylic acids such as naphthenic acids, tall oil acids, rosin acids, etc.

The alkali or alkaline earth metals of the carboxylate reactants may be any which form a carboxylate which is soluble in the organic liquid, but which form a relatively insoluble precipitate with the anion of the gold salt reactant in the same organic liquid. The expression "relatively insoluble precipitate" is defined herein to mean that the alkali or alkaline earth metal salt is sufficiently insoluble to drive the reaction in favor of gold carboxylate formation. Generally the organic liquid is selected such that the solubility of the alkali or alkaline earth metal salt is not more than 1.0 gram per 100 grams of the organic liquid. Preferably, the solubility of the alkali or alkaline earth metal salt formed during the reaction process is not more than about 0.001 gram per 100 grams of organic liquid, and preferably the solubility is not more than about 0.0001 gram per 100 grams of organic liquid. Published solubility data, such as the solubility data compiled in Linke, *Solubilities: Inorganic and Metallo-Organic Compounds,* 4th ed. (Amer. Chem. Soc'y. 1965) may be utilized to select appropriate cation, anion and organic liquid combinations. This reference is hereby fully incorporated herein by reference as it relates to such solubility data. Examples include sodium and potassium carboxylates combined with at least one gold halide in organic liquids such as the acid corresponding to the carboxylate moiety, another carboxylic acid, acetone, tetrahydrofuran, etc.

The reaction between the starting gold salt and the organic carboxylate can generally be carried out at temperatures of from about 0° C. to about 150° C. for a period of time sufficient to form the desired gold carboxylates as long as condition (B) above is met. Generally, the reaction temperature will be at least about 20° C., and often at least about 45° and will generally be not more than about 100° C., and often not more than about 80° C. A temperature of about 56° C. presently is preferred when the organic liquid is acetone, since that is the reflux temperature of acetone at atmospheric pressure. Generally, the reaction will be completed within about 24 hours, and often will be substantially complete within about 6 hours of when it is initiated. Reaction times within about 4 hours can be used to achieve a gold carboxylate product yield of at least 80 wt. % in most cases. Yields as high as 90 wt. % or higher can often be achieved. The period of time required for reacting the gold salt with any particular carboxylate in solution can be readily determined by one skilled in the art.

After the reaction is completed, the organic liquid generally is filtered to remove any undesirable solids which may be present. The filtrate is a solution containing the desired gold carboxylates. Depending on the amount of organic liquid used in the reaction, the filtrate may be concentrated under vacuum to provide solutions having higher concentrations of the gold carboxylate.

In another embodiment of the present invention, the gold carboxylate is prepared by the above-described steps (A), and (B), and optional steps of (C) filtering the product of (B) and recovering the filtrate and (D) evaporating the organic liquid of (A)(3) from the filtrate and redissolving the filtrate in a second organic liquid different from the organic liquid of (A)(3).

In a preferred embodiment, steps (A), (B), (C) and (D) are followed by the further steps of (E) filtering the solvent containing the dissolved filtrate residue.

Steps (C) and (D), and optionally (E), further refine the product obtained in steps (A) and (B) by utilizing an organic liquid which is a good solvent for the gold carboxylate in step (D) relative to contaminants such as the alkali and alkaline earth metal salts produced as a byproduct. In one embodiment of the present invention, the organic liquid of (A)(3) is a ketone and the second organic liquid of (D) is an aromatic solvent. The steps in one preferred embodiment utilize acetone as the organic liquid in (A)(3) and xylene as the second organic liquid in (D).

Contrary to the requirements of (A)(3), the second organic liquids of (D) are not necessarily solvents for the reactants of (A), namely the alkali or alkaline earth metal carboxylates and the starting gold salt, unless it is desirable to provide conditions for continued reaction between the reactants as in steps (A) and (B).

In yet another embodiment of the present invention an organic liquid may be used in the reaction step that has a sufficiently high boiling point that it would be difficult to remove the organic liquid from the gold carboxylate by heating and reducing pressure without decomposing the gold carboxylate. In that case, it may be desirable to conduct the reaction in a minimum amount of the high boiling solvent and then rinse the reaction vessel, precipitates, and filter medium with a volatile gold carboxylate solvent into the filtrate solution. Heat and/or reduced pressure can then be used to remove the volatile solvent without decomposing the gold carboxylate. One example of such a protocol would be to conduct the reaction in 2-ethylhexanoic acid and rinse the reaction vessel, precipitates and filter medium with pentane, collecting the wash, and evaporating the pentane to concentrate the gold carboxylate in the filtrate.

The amount of alkali or alkaline earth metal salt of an organic carboxylic acid added to the mixture in step (A) is not critical. Similarly, the concentration of the starting gold salt in the mixture prepared in step (A) is not critical and may be varied over a wide range. Generally, the concentration of the starting gold salt will be from about 1 to about 40% by weight, preferably from about 10 to about 20% by weight. Typically, the reactants are mixed in about stoichiometric amounts, but in some instances an excess of a reactant may be used to force the reaction to completion. Generally, the molar ratio of alkali or alkaline earth metal carboxylate to starting gold salt is in the range from about 1:1 to about 10:1.

The amount of organic liquid added to the mixture in step (A) should be an amount which will yield a solution of the desired gold carboxylate in acceptable concentration. Generally, the solutions of the gold salts of organic carboxylic acids obtained in accordance with the present invention preferably contain at least about 3 wt. %, and more preferably at least about 6 wt. %, gold. The concentration of PGM and/or rhenium can approach the theoretical limit that may be present in the formulae for the carboxylate salts sans solvent in which the number of equivalents of PGM and/or rhenium equals the number of equivalents of the carboxylate. Concentrations up to about 50% by weight or higher of gold can be obtained. Typically, the metal concentration is at least up to about 30% by weight. The organic phase containing organic liquid and the gold carboxylates can be further diluted with solvent to provide solutions containing a desired concentration. The organic solvent can be stripped from the gold carboxylate so that the gold carboxylate can be used neat or redissolved in a completely different solvent, such as in above-described optional step (D), when the organic liquid or solvent is sufficiently volatile. The solutions may be filtered to remove suspended particles.

The following example illustrates the process of the present invention and gold carboxylate solutions which are prepared in accordance with the process of the invention. Unless otherwise indicated in the following example and elsewhere in the specification and claims, all parts and percentages are by weight, all temperatures are in degrees Celsius, and all pressures are at or near atmospheric.

EXAMPLE 1

5.23 grams of gold trichloride, 9.05 grams of sodium 2-ethylhexanoate and 12.1 grams of 2-ethylhexanoic acid are mixed in a reaction flask. The mixture is warmed to 50° C. and stirred for 30 minutes. The slurry which forms is then filtered and the reaction flask and filter funnel are rinsed with pentane in portions which total about 50 mL. The filtrate is then warmed to 50° C. under a mild vacuum to evaporate the pentane. The product is a clear yellow solution containing 3.27 grams of gold. Yield is 96%.

The stability of the products prepared in accordance with this invention can be improved by incorporating various solubilizing and stabilizing agents such as, for example, ammonia, amines, chelating agents, amounts of at least one of the above-described organic carboxylic acids in excess of the amount required for the gold carboxylate, etc.

The gold salts of carboxylic acids prepared in accordance with the present invention can be recovered and isolated as crystalline solids, waxy solids, or oils depending on the specific carboxylate used. The techniques for recovering these products from the solutions of the present invention are well known in the art, such as by precipitation, evaporation, etc. Gold carboxylates can be thermally decomposed at temperatures of about 250° C. or lower to form gold, and often at temperatures of about 170° C. or less. Such low decomposition temperatures are advantageous for applying gold to temperature-sensitive materials such as plastic and other organic polymeric materials. This ability is particularly desired in the electronics industry.

The gold carboxylates and gold carboxylate solutions prepared in accordance with the present invention also are characterized as being substantially free of sulfur atoms and chloride, nitrate and other anions when such atoms are avoided as hetero atoms in the above-described R group. The absence of sulfur prevents the emission of the objectionable noxious odors generally associated with the decomposition of commerically available gold-containing materials, particularly in connection with decorative and electronic applications. The gold carboxylate products of the present invention generally have about 0.1 weight-percent or less sulfur present, and typically contain 10 ppm or less sulfur when utilized in such applications.

The ability to form high concentration organic gold solutions also has an advantage over certain pastes now used which contain finely divided gold particles in that a uniform thin coating of gold may be applied. This advantage is particularly valuable in the electronics field and in the application of gold coatings on glass, ceramics, and plastic.

As mentioned above, the gold carboxylates of the present invention can be produced substantially free of undesired cations such as chloride, nitrate and other anions. An added benefit of the absence of such anions can be the avoidance of undesired generation of corrosive compounds generated during or after decomposition of metallo-organo films produced from the carboxylates of the present invention. Examples of such corrosive compounds include hydrogen chloride gas, hydrochloric acid, nitrous oxides and nitric acid. The benefit of avoiding such corrosive compounds may be most noticeable when the metallo-organo films made from the carboxylates of the present invention are used in proximity to sensitive components such as electronic components and acid-sensitive substrates.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of preparing gold salts of organic acids comprising
   (A) preparing a mixture of
      (1) at least one alkali or alkaline earth metal salt of an organic carboxylic acid comprising at least 2 carbon atoms,
      (2) at least one gold salt having an anion other than the carboxylate anion of (A)(1), and
      (3) an organic liquid capable of at least partly dissolving the at least one alkali or alkaline earth metal salt of an organic carboxylic acid (1) and the at least one gold salt (2), but wherein a salt formed between the alkali or alkaline earth metal of (1) and the anion of (2) in the mixture is sufficiently insoluble in the organic liquid to drive the reaction in favor of the formation of the gold salt of the carboxylic acid; and
   (b) maintaining the mixture (A) at a temperature below the decomposition temperature of components (1), (2) and (3) and gold carboxylated product for a period of time sufficient to form the gold carboxylate.

2. The method of claim 1 wherein the organic liquid comprises a ketone, a hydroxy-containing organic compound, an aromatic hydrocarbon, or a saturated ether, or a mixture thereof.

3. The method of claim 1 wherein the organic liquid comprises acetone, methyl ethyl ketone, ethanol, propanol, xylene or tetrahydrofuran, or a mixture thereof.

4. The method of claim 1 wherein said alkali or alkaline earth metal salt of an organic carboxylic acid (1) comprises at least one aliphatic carboxylic acid containing from about 4 to about 30 carbon atoms.

5. The method of claim 1 wherein the metal of said alkali or alkaline earth metal salt of an organic carboxylic acid is an alkali metal.

6. The method of claim 1 wherein the gold salt comprises gold trichloride or tetrachloroauric acid, or a mixture thereof.

7. The method of claim 1 conducted at a temperature in the range from about 20° to about 100° C.

8. The method of claim 1 further comprising
   (C) filtering the product produced in (B) and recovering the filtrate.

9. The method of claim 8 further comprising
   (D) evaporating the organic liquid of (A)(3) from the filtrate to form a filtrate residue; and
   (E) treating the filtrate residue with a second organic liquid different from the organic liquid of (A)(3).

10. The method of claim 9 further comprising
    (F) filtering the second organic liquid containing the dissolved filtrate residue.

11. The method of claim 10 wherein the filtrate contains at least 80 weight-percent gold carboxylate yield.

12. The method of claim 10 wherein the filtrate contains at least 90 weight-percent gold carboxylate yield.

13. The method of claim 11 wherein at least about 80 weight-percent of the organic carboxylic acid of (A)(1)

is at least one aliphatic carboxylic acid having from 6 to about 30 carbon atoms.

14. The method of claim 1 wherein the ratio of the alkali or alkaline earth metal of an organic acid (1) to the gold salt (2) in (A) is in the range from about 1:1 to about 10:1.

15. A method of preparing gold salts of an organic acid consisting essentially of the steps of:
   (A) preparing a mixture of
      (1) at least one alkali or alkaline earth metal salt of an organic carboxylic acid having from about 2 to about 30 carbon atoms,
      (2) at least one gold chloride, and
      (3) an organic liquid capable of at least partially dissolving the at least one alkali or alkaline earth metal salt of an organic carboxylic acid (1) and the at least one gold chloride (2), but wherein a salt formed between the alkali or alkaline earth metal of (1) and the chloride of (2) in the mixture is sufficiently insoluble in the organic liquid to drive the reaction in favor of the formation of the gold salt of the carboxylic acid; and
   (B) maintaining the mixture (A) at a temperature in the range from about 0° to about 150° C. for a period of time sufficient to form the gold carboxylate.

16. The method of claim 15 wherein the carboxylic acid of (A)(1) comprises at least one aliphatic carboxylic acid having from about 6 to about 18 carbon atoms.

17. The method of claim 15 wherein the organic liquid comprises a ketone.

18. The method of claim 15 wherein the gold chloride comprises gold trichloride and the organic liquid comprises acetone.

19. The method of claim 15 wherein the temperature of the mixture (B) is maintained in the range from about 45° to about 80° C.

20. The method of claim 15 further comprising:
   (C) filtering the product of (B) and recovering the filtrate;
   (D) evaporating the organic liquid of (A)(3) from the filtrate to form a filtrate residue; and
   (E) treating the filtrate residue with a second organic liquid different from the organic liquid of (A)(3) to dissolve the desired gold carboxylate.

21. The method of claim 20 wherein the organic liquid of (A)(3) comprises a ketone and the second organic liquid of (D) comprises a hydroxy-containing organic compound.

22. The method of claim 20 wherein the organic liquid of (A)(3) is acetone and the second organic liquid of (D) is xylene.

23. The method of claim 15 wherein the alkali or alkaline earth metal of (A)(1) comprises sodium or potassium.

24. The method of claim 15 wherein the alkali or alkaline earth metal salt of a carboxylic acid of (A)(1) is an alkali or alkaline earth metal salt of propionic acid, butyric acid, isopentanoic acid, hexanoic acid, 2-ethylbutyric acid, nonanoic acid, decanoic acid, 2-ethylhexanoic acid, isooctanoic acid, isononanoic acid, neodecanoic acid, dodecanoic acid, lauric acid, palmitic acid, stearic acid, oleic acid, linoleic acid, naphthenic acids, tall oil acids, or rosin acids, or a mixture thereof.

25. The method of claim 15 wherein the alkali or alkaline earth metal salt of a carboxylic acid of (A)(1) comprises an alkali or alkaline earth metal salt of neodecanoic acid.

* * * * *